United States Patent [19]

Karsten

[11] 3,931,032
[45] Jan. 6, 1976

[54] ANTIBACTERIAL AND GERMICIDAL N,N-DIALKYLTHIOCARBAMOYL SULFENAMIDE DETERGENT COMPOSITIONS

[75] Inventor: Kenneth S. Karsten, Westport, Conn.

[73] Assignee: R. T. Vanderbilt Company, Inc., East Norwalk, Conn.

[22] Filed: Oct. 1, 1973

[21] Appl. No.: 402,313

[52] U.S. Cl. ............ 252/107; 252/106; 260/247.1; 260/551; 424/248; 424/320
[51] Int. Cl.² ...................... C11D 3/48; C11D 9/50
[58] Field of Search ........... 252/106, 107; 424/248, 424/267, 300, 320–321, 328; 260/567, 551, 247.1, 294.8

[56] References Cited
UNITED STATES PATENTS

| | | | |
|---|---|---|---|
| 2,269,893 | 1/1942 | Carter | 424/248 |
| 2,424,921 | 7/1947 | Smith et al. | 260/551 |
| 2,432,255 | 12/1947 | Skaptason | 260/551 |
| 2,692,862 | 10/1954 | Lipsitz | 252/107 |
| 2,910,497 | 10/1959 | Meuly | 260/455 |
| 2,927,899 | 3/1960 | Goldwasser | 252/107 |
| 2,972,627 | 2/1961 | Garmaise et al. | 260/455 |
| 3,423,416 | 1/1969 | Hyatt | 260/294.8 |
| 3,565,894 | 2/1971 | D'Amico | 260/247.1 |

FOREIGN PATENTS OR APPLICATIONS
1,235,919   6/1960   France

*Primary Examiner*—P. E. Willis, Jr.
*Attorney, Agent, or Firm*—Roland T. Bryan

[57] ABSTRACT

Antibacterial and germicidal detergent compositions contain as an active ingredient N,N-dialkylthiocarbamoyl sulfenamides of the formula

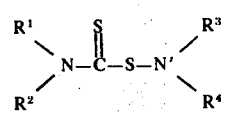

where $R^1$ and $R^2$ represent lower alkyl groups, both $R^3$ and $R^4$ are cyclohexyl or $R^3$ is hydrogen when $R^4$ is phenyl and compounds where $R^1$ and $R^2$ as well as $R^3$ and $R^4$ form a heterocyclic ring, particularly morpholine. The active compounds are particularly useful as skin substantive bacteriostats in soap and shampoo formulations and as germicides in cosmetic and toilet preparations.

6 Claims, No Drawings

ANTIBACTERIAL AND GERMICIDAL N,N-DIALKYLTHIOCARBAMOYL SULFENAMIDE DETERGENT COMPOSITIONS

BACKGROUND OF THE INVENTION

1. Field of the Invention

The present invention relates to the use of certain N,N-dialkylthiocarbamoyl sulfenamides as bacteriostats and germicides and more particularly to their use as active ingredients in detergent compositions used for skin cleansing. The detergent compositions find advantageous applicability in cosmetic and toilet preparations including shaving creams, cosmetic cleansing creams, hair treatment preparations and the like as well as in medicinal and germicidal bar and liquid soaps and shampoos.

2. Description of the Prior Art

The use of compounds such as N,N-dialkylthiocarbamoyl mono- and dicycloalkylsulfenamides and N,N-dialkylthiocarbamoyl mono- and diarylsulfenamides as fungicides is described in U.S. Pat. No. 2,432,255. U.S. Pat. No. 2,692,862 states that disinfectant soaps and synthetic detergents of anit-bacterial activity and skin retentivity may be obtained by incorporating into cleansing compositions alkyl derivatives of thiocarbamoyl sulfenamides of the formula:

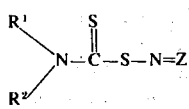

wherein $R_1$ and $R_2$ are the same or different alkyl radicals having not more than 2 C-atmos each, while N=Z is a radical of the group obtained by removing 1 N-attached H-atom from ammonia, a primary or secondary alkyl amine, morpholine and piperidine, the alkyl radicals in the alkyl amine containing not more than 4 C-atoms each.

Thiosulfenyl dithiocarbamates as fungicides are disclosed in U.S. Pat. No. 2,598,989 wherein the patentee also states that even a slight variation in the basic structure or composition of the functional group will often, if not actually always, destroy the fungicidal efficacy of the particular compounds. Variation in or substitution of so-called non-functional or inactive groups or substituents may change the degree of efficacy, making the compound more or less valuable as a fungicidal substance.

Thus, the prior art thiocarbamoyl sulfenamides disclosed as bactericides and fungicides may be considered as being specific and unsuggestive of other combination of substituents providing unpredictable properties, especially in different applications.

SUMMARY OF THE INVENTION

It has been found that certain N,N-dialkylthiocarbamoyl sulfenamides unexpectedly possess specific antibacterial properties and that these properties are advantageously retained in the presence of detergents. Furthermore, the compounds of this invention possess effective skin substantivity, i.e., the property of remaining on the skin and retaining antibacterial and germicidal activity over a period of time after washing, and rinsing of the skin. Besides antibacterial properties, the compounds of this invention possess other desirable properties that are important in their commercial use. For illustration, after inclusion of the compounds of this invention in a detergent composition, the detergent bar, powder, paste or liquid possesses the following properties: initial whiteness, color stability under aging and sunlight exposure and absence of discoloration in the presence of copper.

The aforementioned advantages of this invention are achieved by providing antibacterial and germicidal detergent compositions containing as an active ingredient N,N-dialkylthiocarbamoyl sulfenamides of the formula

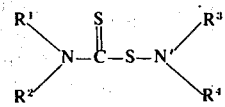

where $R^1$ and $R^2$ represent methyl and ethyl groups, both $R^3$ and $R^4$ are cyclohexyl, compounds where $R^1$ and $R^2$ are methyl and $R^3$ is hydrogen when $R^4$ is phenyl and compounds where $R^1$ and $R^2$ as well as $R^3$ and $R^4$ form a heterocyclic ring, particularly morpholine. Therefore, it is an object of this invention to provide microorganism inhibiting methods and detergent compositions displaying antibacterial and germicidal activity on the skin even after repeated washing and rinsing of the skin.

The term "detergent" is intended to include soap as well as non-soap surface-active agents of the anionic, cationic, nonionic and amphoteric type. Furthermore, the term detergent is intended to cover all products in which soap is a major constituent, for example bar soap, liquid soaps, shaving creams, cosmetic cleansing creams, hair treatment preparations such as shampoos and similar formulations.

A further object of this invention is the provision of shampoo or detergent compositions containing the N,N-dialkylthiocarbamoyl sulfenamides compounds of the invention that are substantive to the skin and that give prolonged effect in reducing the number of microorganisms on skin.

Other objects and advantages will become apparent from the detailed description which follows.

DESCRIPTION OF THE PREFERRED EMBODIMENTS

The compounds of this invention are prepared by general known methods. See, for example, U.S. Pat. No. 2,333,468 describing the oxidative condensation of dithiocarbamic acids and primary or secondary amines to yield N,N-dialkylthiocarbamoyl sulfenamides. To further illustrate, N,N-dimethylthiocarbamoyl-N', N'-dicylohexylsulfenamide is prepared as follows:

A mixture of 100 ml $CCl_4$, 39.6g 25% aqueous solution of dimethylamine and 36.2g dicyclohexylamine is placed in a reaction vessel and cooled to 10°C. 114 ml of 14% aqueous solution of NaOCl is added and the mixture is stirred for 15 minutes at 10°–15°C. After addition of 200 ml $NaHCO_3$—$Na_2CO_3$ buffer solution, the mixture is warmed to 20°C and admixed with 15.2g $CS_2$ with stirring. The mixture is agitated for 40 minutes at 32° – °C. After settling, the nonaqueous phase is separated out and filtered. $CCl_4$ is evaporated by heating under reduced pressure. The residual liquid is added to 150 ml methanol resulting in a precipitation of a solid. The methanol slurry is cooled to 10°C and filtered. The recovered solid is white crystalline material having a melting point of 80°–2°C. The yield is 44.1g.

Relatively small amounts of the antibacterial agents are sufficient to obtain the advantages of the invention. Satisfactory results are obtained when the weight of the antibacterial agent is from 0.1 to 5 percent of the total weight of the detergent composition. The preferred range is 1 to 3 percent based on the weight of the detergent composition. However, it should be understood that greater amounts will be effective but without further substantial advantages. Those skilled in the art will be able to determine, according to known practice, what the effective amount for a given application and/or desired germicidal or biostatic effect must be.

The germicidal agents of this invention can be added to soap or other alkaline skin cleaning agent by any of the common employed methods which result in a uniform distribution of the antibacterial agent throughout the entire mass. Shampoo and soap formulations can, of course, contain any of the usual additives such as coloring agents, perfume, thickeners, solvents, opacifiers, suds builders, conditioning agents, preservatives, buffers, and anti-static agents. The detergent may be soap as well as non-soap surface active agents of the anionic, cationic, nonionic and amphoteric type.

Anionic detergents include both the soap and non-soap detergents. Examples of suitable soaps are the sodium, potassium, ammonium and alkanolammonium salts of higher fatty acids ($C_{10}$–$C_{20}$). Particularly useful are the sodium and potassium salts of the mixtures of fatty acids derived from coconut oil and tallow. Examples of anionic non-soap detergents are alkyl glyceryl ether sulfonates, alkyl sulfates, alkyl monoglyceride sulfates or sulfonates, alkyl polyethoxy ether sulfates, acyl sarcosinates, acyl esters of isothionates, acyl N-methyl taurides, alkyl benzene sulfonates, and alkyl phenol polyethoxy sulfonates. In these compounds the alkyl and acyl groups, respectively, contain 10 to 20 carbon atoms. They are used in the form of water-soluble salts, the sodium, potassium, ammonium and alkanolammonium salts, for example. Specific examples are sodium lauryl sulfate, potassium N-methyl lauroyl tauride; and triethanolamine dodecyl benzene sulfonate.

Suitably useful cationic detergents are exemplified by dilauryldimethyl ammonium chloride, diisobutyl phenoxy ethoxy dimethylbenzyl ammonium chloride, cetyl trimethyl ammonium bromide, N-cetylpyridinium bromide and benzethonium chloride, which are classed as quaternary ammonium salts.

Suitable examples of amphoteric detergents are alkyl beta-iminodipropionates, and alkyl beta-amino propionates, wherein the alkyl group contains 10 to 20 carbon atoms, and basic quaternary ammonium compounds derived from 2-alkyl-substituted imidazoline.

The properties of the preferred embodiments of the invention were evaluated and the results are set forth in the following examples and tables.

EXAMPLE 1 a. Soap Plug Test

Bacteriostatic activity per se was tested by milling into Ivory soap (made according to U.S. Pat. No. 2,295,594) 1 percent test material based on the weight of the soap and by compressing it into plugs. Plugs (0.5 inch in diameter and 0.25 inch thick) of each of the test soaps were placed on agar plates seeded with one of three representative test bacteria, Bacillus subtilis, Staphylococcus aureus, and Salmonella typhosa. After incubation at 37°C. for 24 hrs., the clear zone of inhibition (lack of bacterial growth) was measured and reported as average diameter of zone inhibition (diameter of clear zone less the diameter of the soap plug), and tabulated in Table IA.

b. Hide Substantivity (soap)

For the test of substantivity or retention of bacteriostat by the skin after washing with the test soap, untanned calf-skin hide buttons were soaked in an 8 percent solution of the test soap containing 1% bacteriostat, rinsed four times with distilled water, placed on seeded agar plates and incubated for 24 hrs., at optimum temperature of the test bacteria, Bacillus subtilis, Staphylococcus aureus and Salmonella typhosa. The zones of inhibition was measured and reported as in the soap plug test, and tabulated in Table IA.

The results set forth in Table IA demonstrate the good microorganism inhibiting and skin substantive properties possessed by the compositions of this invention. Moreover, the unexpected effectiveness of the thiocarbamoyl sulfenamides of this invention in detergent compositions is apparent from comparison with the ineffectiveness of structurally similar compounds. Employing the identical test procedure previously described, bacteriostatic activity for some thiocarbamoyl sulfenamides not falling within the formula of this invention was evaluated. The results, tabulated in Table IB, demonstrate a lack of substantial bacteriostatic activity and substantivity in soap for these related compounds and thus the unpredictability of useful efficacy.

TABLE IA

BACTERIOSTATIC ACTIVITY AND SUBSTANTIVITY IN SOAP

Average Diameter of Inhibited Zone in MM

| Active Ingredients | (a) Activity in Soap | | | (b) Hide Substantivity in Soap | | |
|---|---|---|---|---|---|---|
| | B. subtilis | S. aureus | S. typhosa | B. subtilis | S. aureus | S. typhosa |
| N,N-Dimethylthiocarbamoyl-N′,N′-dicyclohexylsulfenamide | 12 | 12 | 10 | 3 | 4 | 2 |
| N,N-Diethylthiocarbamoyl-N′,N′-dicyclohexylsulfenamide | 15 | 16 | 12 | 2 | 3 | 2 |
| N,N-Dimethylthiocarbamoyl-N′-phenyl-sulfenamide | 24 | 22 | 19 | 3 | 6 | 2 |
| N,N,N′,N′-Bis(2,2′-oxydiethylene)-thiocarbamoylsulfenamide | 5 | 12 | 4 | 4 | 10 | 2 |

TABLE IB

THICARBAMOYL SULFENAMIDES WITHOUT SUBSTANTIAL BACTERIOSTATIC ACTIVITY AND SUBSTANTIVITY IN SOAP

| Active Ingredients | Activity in Soap | | | Hide Substantivity in Soap | | |
|---|---|---|---|---|---|---|
| | B. subtilis | S. aureus | S. typhosa | B. subtilis | S. aureus | S. typhosa |
| N,N-di-n-butylthiocarbamoyl-N',N'-dicyclohexylsulfenamide | 6 | 0 | 0 | 0 | 0 | 0 |
| N,N-diethylthiocarbamoyl-N'-phenyl-sulfenamide | 0 | 0 | 0 | 0 | 0 | 0 |
| bis(3,5-dimethyloxydiethylene)-thiocarbamoyl sulfenamide | 0 | 0 | 0 | 0 | 3 | 0 |
| N,N-dieicosylthiocarbamoyl-N',N'-dicyclohexylsulfenamide | 0 | 0 | 0 | 0 | 0 | 0 |

EXAMPLE II

The skin substantivity test was repeated using shampoo formulations as follows:

| Ingredients | Shampoo A Percent By Weight | Shampoo B Percent By Weight |
|---|---|---|
| Sodium salt of sulfated coconut fatty alcohol | 23 | — |
| Sodium stearate | 8.7 | — |
| Sodium alkyl glyceryl ether sulfonate[1] | — | 28.3 |
| Sodium acyl sarcosinate[2] | — | 5.0 |
| Sodium sulfate | 0.8 | 2.6 |
| Sodium chloride | — | 6.6 |
| Trisodium phosphate | 2.1 | — |
| Diethanolamide of coconut fatty acids | — | 2.0 |
| Perfume | 1.0 | 0.4 |
| Active Ingredient | 2.0 | 2.0 |
| Water, made up to 100% | — | — |
| pH | 7.7 | 7.4 |

[1]alkyl radicals derived from fatty alcohol, 25.3% from coconut and 3% from tallow

[2]acyl radicals derived from coconut fatty acids

Untanned calf-skin buttons were soaked in an 8 percent solution of the test shampoo containing 2% bacteriostat, rinsed four times with distilled water, placed on seeded agar plates and incubated for 24 hrs. at optimum temperature of the test bacteria, *Bacillus subtilis*, *Staphylococcus aureus* and *Salmonella typhosa*. The zones of inhibition were measured and reported as in the soap plug test and tabulated in TABLE II.

40 hrs. Upon comparison to the unexposed portion of the soap, no color change was observed.

Thus, there have been disclosed N,N-dialkylthiocarbamoyl sulfenamides which unexpectedly possess excellent germicidal and substantive properties which are retained in the presence of detergents. These properties, as well as the color stability of the compounds of the invention, indicate the applicability of the compounds as active ingredients in germicidal or medicinal soaps, shampoos and other skin-cleansing compositions.

I claim:

1. A skin-substantive microorganism-inhibiting cleansing composition comprising a synthetic organic detergent selected from the group consisting of anionic, nonionic cationic and amphoteric detergents and fatty acid soaps, and a biostatically effective amount of a compound of the general formula:

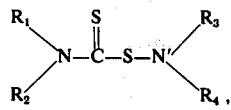

said compound being selected from the group consisting of compounds wherein (1) $R_1$ and $R_2$ are methyl or ethyl, $R_3$ and $R_4$ are cyclohexyl; (2) $R_1$ and $R_2$ are methyl and $R_3$ is hydrogen when $R_4$ is phenyl; and (3) $R_1$ with $R_2$ and $R_3$ with $R_4$ form heterocyclic rings.

2. A skin substantive microorganism inhibiting

TABLE II

HIDE SUBSTANTIVITY IN SHAMPOO

| Active Ingredient | Shampoo Composition | Average Diameter of Inhibited Zone in MM | | |
|---|---|---|---|---|
| | | B. subtilis | S. aureus | S. typhosa |
| N,N-Dimethylthiocarbamoyl-N',N'-dicyclohexylsulfenamide | A | 4 | 0 | 2 |
| do. | B | 11 | 11 | 13 |
| N,N-Dimethylthiocarbamoyl-N'-phenyl-sulfenamide | A | 10 | 8 | 5 |
| do. | B | 18 | 20 | 14 |
| N,N,N',N'-Bis(2,2'-oxydiethylene)thio-carbamoylsulfenamide | A | 14 | 14 | 9 |
| do. | B | 12 | 13 | 11 |
| N,N-Diethylthiocarbamoyl-N',N'-dicyclohexyl-sulfenamide | A | 11 | 11 | 3 |
| do. | B | 12 | 10 | 6 |

EXAMPLE III

To test the color stability of detergent compositions, a soap plug containing N,N-dimethylthiocarbamoyl-N', N'-dicyclohexylsulfenamids as active ingredient was cut in two, and one portion was exposed to sunlight for cleansing composition as claimed in claim 1 wherein the heterocyclic ring formed by $R_1$ and $R_2$, and $R_3$ and $R_4$ is morpholine.

3. A skin substantive microorganism inhibiting cleansing composition as claimed in claim 1 wherein the biostatically effective amount is 0.1 to 5 percent of the total weight of the composition.

4. A skin substantive microorganism inhibiting cleansing composition as claimed in claim 3 wherein the detergent is a shampoo.

5. A biostatically active, skin substantive detergent composition comprising at least one synthetic organic detergent selected from the group consisting of anionic, nonionic, cationic and amphoteric detergents and fatty acid soaps, and a biostatically effective amount of an active agent selected from the group consisting of N,N-dimethylthiocarbamoyl-N',N'-dicyclohexylsulfenamide, N,N-diethylthiocarbamoyl-N',N'-dicyclohexylsulfenamide, N,N-dimethylthiocarbamoyl-N'-phenylsulfenamide and N,N,N', N'-bis(2,2'-oxydiethylene) thiocarbamoylsulfenamide.

6. A method of inhibiting skin microorganisms comprising applying thereto a cleansing agent composition including at least one synthetic organic detergent selected from the group consisting of anionic, nonionic, cationic and amphoteric detergents and fatty acid soaps and from 0.1 to 5 percent of the total weight of the composition of a compound of the general formula

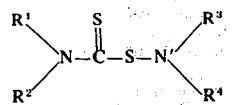

where the compound is selected from the group consisting of compounds were (2) $R_1$ and $R_2$ are methyl or ethyl, $R_3$ and $R_4$ are cyclohexyl; (2) $R_1$ and $R_2$ are methyl and $R_3$ is hydrogen when $R_4$ is phenyl; and (3) $R_1$ and $R_2$ and $R_3$ and $R_4$ form a heterocyclic ring.

* * * * *

UNITED STATES PATENT OFFICE
CERTIFICATE OF CORRECTION

Patent No. 3,931,032      Dated January 6, 1976

Inventor(s) Kenneth S. Karsten

It is certified that error appears in the above-identified patent and that said Letters Patent are hereby corrected as shown below:

Column 1, line 24, change "anit-bacterial" to --antibacterial--;

line 36, change "C-atmos" to --C-atoms--.

Column 2, line 64, before "°C" insert --5--.

Column 3, line 36, change "isothionates" to --isethionates--;

line 48, after "ethoxy" insert --ethyl--.

Column 5, lines 67 and 68, change "N,'N'-dicyclohexylsulfenamids"

to --N,N'-dicyclohexylsulfenamide--.

Column 6, line 31, after "nonionic" insert a comma.

Column 8, line 14, change "(2)" to --(1)--.

Column 8, line 14, "were" should read --where--.

Signed and Sealed this twentieth Day of April 1976

[SEAL]

Attest:

RUTH C. MASON  
Attesting Officer

C. MARSHALL DANN  
Commissioner of Patents and Trademarks